United States Patent [19]

Velati Bellini et al.

[11] Patent Number: 5,728,571
[45] Date of Patent: *Mar. 17, 1998

[54] **EXPRESSION AND SECRETION OF MATURE HUMAN BETA INTERLEUKIN-1 IN *BACILLUS SUBTILIS* AND MEANS AND METHODS FOR ITS ACHIEVEMENT**

[75] Inventors: Ada Velati Bellini, Pavia; Giuliano Galli; Giuseppe Lucchese, both of Monterotondo; Guido Grandi, Segrate, all of Italy

[73] Assignee: Eniricerche S.p.A., Milan, Italy

[*] Notice: The term of this patent shall not extend beyond the expiration date of Pat. No. 5,437,988.

[21] Appl. No.: 405,775

[22] Filed: Mar. 17, 1995

Related U.S. Application Data

[62] Division of Ser. No. 72,692, Jun. 7, 1993, Pat. No. 5,437,988, which is a continuation of Ser. No. 554,755, Jul. 19, 1990, abandoned.

[30] Foreign Application Priority Data

Jul. 19, 1989 [IT] Italy ........................... 21228/89

[51] Int. Cl.⁶ .................... C12N 1/21; C12N 15/63; C12N 15/67; C12N 15/75
[52] U.S. Cl. ..................... 435/252.31; 435/69.8; 435/172.3; 435/320.1; 435/839; 536/24.1
[58] Field of Search .................. 435/69.1, 69.8, 435/252.31, 320.1, 839, 172.3; 536/24.1; 935/27, 29, 41, 48

[56] References Cited

U.S. PATENT DOCUMENTS 5,015,574  5/1991  Furutani et al. ................ 435/67.1

FOREIGN PATENT DOCUMENTS

| 0213085 | 3/1987 | European Pat. Off. . |
|---|---|---|
| 213085 | 3/1987 | European Pat. Off. . |
| 0252561 | 1/1988 | European Pat. Off. . |
| 306673 | 3/1989 | European Pat. Off. . |
| 0353516 | 2/1990 | European Pat. Off. . |
| 0251158 | 4/1987 | Germany . |
| 2171703 | 9/1986 | United Kingdom . |

OTHER PUBLICATIONS

A. Nakayama et al. "Processing of the Prepropeptide Portions of the *Bacillus amyloliquefaciens* Neutral Protease . . . " *Journal of Biotechnology* Sep. 3, 1991, pp. 55-69.

S.T. Motley et al. "Expression & Secretion of Human IL-1 in *B. subtilis*" *Genetics & Biotechnology of Bacilli* 2: 371-375 (1988).

*Primary Examiner*—Dian C. Jacobson
*Attorney, Agent, or Firm*—Sughrue, Mion, Zinn, Macpeak & Seas

[57] ABSTRACT

A new plasmid vector is described which can replicate in *B. subtilis* and which can express and secrete, in the culture medium, human beta interleukin-1 (beta IL-1) without amino acid sequences extraneous to the natural molecule, a strain of *B. subtilis* transformed by the vector and a method for the expression and secretion of mature human beta interleukin-1. The human beta interleukin-1 thus obtained shows a specific acitvity of $1\times10^9$ U/mg of protein and is particularly suitable as a stimulant for the immune system, as an adjuvant in vaccines for the activation of the repair mechanism in cases of tissue damage, and for the treatment of auto-immune diseases in man.

6 Claims, 9 Drawing Sheets

```
EcoRI   MET ARG SER LYS LYS LEU TRP ILE SER LEU LEU PHE ALA LEU THR LEU ILE PHE THR MET ALA PHE SER ASN MET
AATTCTTATGAGAAGCAAAAAATTGTGGATCAGCTTGTTGTTTGCGTTAACGTTAATCTTACGATGGCATTCAGCAACATG
GAATACTCTTCGTTTTTTAACACCTAGTCGAACAACAAACGCAATTGCAATTAGAAATGCTACCGTAAGT            5'
                                    LEADER   SUBTILISINA
5'
```

FIG. 4

EXPRESSION AND SECRETION OF MATURE HUMAN BETA INTERLEUKIN-1 IN *BACILLUS SUBTILIS* AND MEANS AND METHODS FOR ITS ACHIEVEMENT

This is a divisional of application Ser. No. 08/072,692 filed 7 Jun. 1993, U.S. Pat. No. 5,437,988, which is a continuation of application Ser. No. 07/554,755 filed 19 Jul. 1990, abandoned.

The present invention relates to the expression and secretion of human beta interleukin-1 without aminoacid sequences extraneous to the natural molecule by *Bacillus subtilis* (*B. subtilis*) cells and means and methods for its achievement.

Human beta interleukin-1, referred to below as beta IL-1 is a protein belonging to the lymphomonokine family which is secreted by activated macrophages. The protein can mediate various biological and immune activities (Mizel, S. D., Immunol. Rev., 63, 51–72, 1982; Durum, S. K. et al., Annu. Rev. Immunol., 3, 263–270, 1984). In fact, by inducing the release of IL-2, beta IL-1 indirectly stimulates the maturation of T cells, and hence the production of antibodies, thus contributing to the amplification of the immune response. Moreover, beta IL-1 stimulates the maturation and proliferation of the B cells and, in cases of tissue damage, contributes to the activation of the repair mechanisms by indirectly promoting the growth of fibroblasts. In view of its many activities, the possibility of using this protein in the treatment of wounds, burns and autoimmune diseases in man seems ever more attractive.

Naturally, this requires the availability not only of adequate quantities of beta IL-1, but also of a very pure product with a high specific activity.

The recent cloning of the gene which codes for this protein has enabled it to be prepared by recombinant DNA techniques. More particularly, the expression of beta IL-1 has been achieved in *Escherichia coli* (*E.coli*) cells engineered both in mature form (March, C. J. et al., Nature, 315, 641–646, 1985; Wingfield, P et al., Eur. J. Biochem., 160, 491–497, 1986; Kronein, S. R. et al., Biotech., 4, 1078–1082, 1986) and as a product fused to the first 24 amino acids of *E.coli* beta galactosidase (Dinarello, C. A. et al. J. Clin. Invest., 77, 1734–1740, 1986).

Methods which use these microorganisms, however, have disadvantages resulting, on the one hand, from the presence of endotoxins produced by *E.coli* and, on the other hand, from the fact that, in some cases, beta IL-1 is produced in an insoluble form. In fact the methods of purification generally used in the art do not enable the complete removal of the endotoxins which, being pathogenic in man, are undesirable products. Moreover, the dissolution of the beta IL-1, which is necessary for its subsequent purification, requires the use of substances such as, for example, urea or guanidinium hydrochloride, which can denature the protein, and consequently reduce its specific activity.

In order to overcome these problems, it has been proposed in the art to use methods for the production of the protein which are based essentially on the use of *B.subtilis*, an organism which is not pathogenic in man and which can secrete the proteins in the culture medium, as the host.

Thus, for example, EP-A-0353516 describes a method for the expression of beta IL-1 by *B.subtilis*. This method, whilst allowing the protein to be made in a soluble and easily-purifiable form, in a single chromatographic step, cannot produce the beta IL-1 outside the cells. Motley, S. T. and Graham, S. (Genetics and Biotech. of Bacilli, vol. 2, pp. 371–375, 1987, Academic Press Inc.) describe a method for the expression and secretion of beta IL-1 by *B.subtilis* including the construction and use of a recombinant vector which contains the penicillinase promoter of *B.licheniformis* fused to the alpha-amylase secretion signal sequence of *B.amyloliquefaciens* modified in vitro so as to contain the Pst I site in the protein maturation region.

This method however, achieves the secretion of beta IL-1 with a yield of 4 µg/ml and with a specific activity less than that of the beta IL-1 obtained by the recombinant DNA technique from *E.coli*.

Moreover, the expression and secretion vector used does not provide the mature protein. In fact, analysis of the amino acids in the molecule secreted shows the presence, at its N-terminal, of two amino acid residues (Ala and Asp) which are extraneous to the natural molecule.

The object of the present invention is, therefore, to establish a method for the expression and secretion of beta IL-1 by *B.subtilis* which does not have the disadvantages described above.

This object is achieved, according to the present invention, by the provision of a new vector which is replicable in *B.subtilis* and can express and secrete mature human beta IL-1.

A subject of the present invention is, therefore, a vector replicable with expression in *B.subtilis* which includes the promoter and the RBS of *B.subtilis* neutral protease and, downstream thereof, specific sites useful for the cloning of heterologous genes.

Another subject of the present invention is a recombinant plasmid vector which can express and secrete mature human beta interleukin-1 in *B.subtilis*.

A further subject of the present invention is a strain of *B.subtilis* transformed by the recombinant plasmid vector.

Another subject of the present invention is a method for the expression and secretion of mature human beta IL-1 which comprises the growth of the aforementioned transformed strain of *B.subtilis* in a suitable culture medium and the separation and purification of the human beta IL-1 thus secreted from the culture medium.

Further subjects of the present invention will become clear from a reading of the description and examples which follow.

In particular, the vector of the present invention with expression in *B.subtilis*, hereinafter indicated pSM 308, contains the CAT gene which codes for resistance to chloramphenicol, the promoter and the RBS of *B.subtilis* neutral protease and, immediately downstream thereof, the EcoRI restriction site and the multiple cloning site (m.c.s.) of pUC 12, which are useful for the insertion of heterologous genes.

The plasmid was produced by a method comprising:

a) the isolation from the plasmid pSM 127 NRRL-B 15900, of the 1500 base-pair (BP) Hind III-Bam HI fragment containing the promoter, the RBS and the first 200 nucleotides of *B.subtilis* neutral protease;

b) the construction, by mutagenesis in vitro, of the EcoRI restriction site immediately downstream of the RBS of the fragment isolated in a) and the removal of the 200 nucleotides of the neutral protease to obtain the DNA fragment with approximately 1300 bp;

c) the isolation from the plasmid pC 194 of the 2400 bp Hind III-Mbo I fragment containing the CAT gene and the replication origin which operates in *B.subtilis*;

d) the ligation, in the presence of T4 DNA ligase, of the fragments obtained in b) and c) to the 50 bp EcoRI-Hind III fragment of pUC 12 which constitutes the multiple cloning site, and, finally, e) the isolation of the vector pSM 308 by the selection of *B.subtilis* cells transformed by the ligation mixture obtained in step d).

The plasmid pSM 308 was constructed with the use of techniques generally known in the field of recombinant DNA.

According to the present invention, the plasmid is particularly useful for the cloning and expression of heterologous genes which code for a protein of interest.

According to one embodiment of the present invention, the plasmid pSM 309 was used to construct the recombinant plasmid vector pSM 320 for the expression and secretion of human beta interleukin-1.

In practice, the plasmid pSM 261 ATCC 67743, which contains the gene which codes for human beta interleukin-1, was linearised by means of the EcoRI restriction enzyme which cuts immediately upstream of the translation-initiation codon ATG. The plasmid DNA was then treated in succession with exonuclease, which hydrolyses the DNA starting from its 5' and 3 terminals. These enzymatic treatments eroded the 5' terminal portion of the gene which codes for human beta interleukin 1 and then exposed the 5' terminal as a single helix. The DNA, thus treated, was then digested with PstI restriction endonuclease which cuts downstream of the stop codon of the beta IL-1 gene, and the 630-bp fragment (B DNA) generated by these treatments was isolated on agarose gel. In order to put this gene under the control of the leader sequence of subtilisin (serinic protease) and achieve the secretion of the mature protein, it was necessary to synthesise an oligonucleotide having a nucleotide sequence identical to that of the leader sequence, in which the 5' end was compatible with that generated by the EcoRI restriction enzyme and the exposed 3' end lacked the last 12 nucleotides which constitute the specific cleavage site. This oligonucleotide, whose nucleotide sequence is given in FIG. 4, was then ligated with the 2700 bp EcoRI-PstI fragment isolated from the plasmid pUC 13, in the presence of T4 DNA ligase. The resulting ligation mixture was digested with the PstI restriction enzyme in order to eliminate any dimers formed.

Finally, the 2780 bp fragment hereinafter indicated A DNA was isolated from the mixture.

In order to bond this fragment to the B DNA isolated as described above, a single-strand, 36 bp oligonucleotide was synthesised, which could form a bridge between the exposed 3' and 5' ends of the A and B DNA and which contained the nucleotides which form the specific cleavage site of subtilisine.

The sequence of this oligonucleotide is (SEQ.ID. No.1):

```
          Asn Met Ser Ala Gln Ala Ala Pro Val Arg Ser
3' CG TTG TAC AGA CGC GTC CGG CGT GGA CAT GCT AGT G 5'
   SUB. LEADER            +1    beta IL-1
```

Finally, the A and B DNA and the synthetic oligonucleotide described above were ligated together in the presence of T4 DNA ligase.

The resulting mixture was Used to transform competent *E.coli* cells and the transformants were selected on a selective culture medium. The plasmid pUC 13 Ls beta IL-1 with approximately 3480 bp and which contained the structural gene of beta IL-1 immediately preceded by the subtilisine secretion-signal sequence was extracted from one of the positive clones. The approximately 700-bp fragment containing the structural gene of beta IL-1 preceded by the subtilisin secretion signal was then isolated from the plasmid by digestion with EcoRI and PstI restriction enzymes. This fragment was then ligated in ligation buffer with the plasmid pSM 308 which had previously been digested with the EcoRI and PstI enzymes. The resulting mixture was then used to transform competent *B.subtilis* cells and the transformants were selected on a suitable culture medium to which chloramphenicol had been added.

A plasmid with approximately 4510 bp, and having the desired characteristics was extracted from one of the positive clones. As confirmed by analysis of its nucleotide sequence by the method of Sanger, F. et al. (PNAS, 74, 5460–5467, 1977), the plasmid (pSM 320) contained the gene for human beta interleukin-1 fused to the subtilisin secretion signal sequence and placed under the control of the neutral protease promoter.

In order to confirm the capacity of this plasmid to express and secrete the protein in mature form, *B.subtilis* cells were transformed thereby.

Various *B.subtilis* strains selected from those generally used in this field may be used for this purpose.

The preferred strains are those which do not produce protease such as, for example, *B.subtilis* SMS 118 (rec$^+$, npr$^-$, spr$^-$).

The transformed microorganisms were grown in a suitable culture medium at approximately 37° C.

The acellular supernatant liquor and the cellular proteinaceous extract were analysed by electrophoresis on polyacrylamide gel and subsequent staining with Coomassie blue ("Gel electrophoresis of proteins: a practical approach"", Ed. B. D. Hames and D. Rickwood IRL Press Ltd.) and immunoblot on nitrocellulose. The results obtained showed the presence of a protein which had a molecular weight of 17,500 daltons, corresponding to that of beta IL-1, and which was capable of reacting specifically with anti-beta-IL-1 antibodies, only in the supernatant liquor, thus confirming that it was secreted completely.

The protein was absent from the cell extracts and the supernatant liquors of the control strains.

In accordance with the present invention, the protein secreted was purified from the culture medium by one of the conventional techniques.

Preferably, the protein was purified by ion-exchange chromatography.

The fractions containing the eluted proteins were collected and analysed by gel electrophoresis on sodium dodecyl sulphate-polyacrylamide (SDS-PAGE) as described by Laemmli (Nature, 227, 680–685, 1970). Those containing beta IL-1, which showed only one narrow band, were recombined and concentrated by filtration through a membrane.

The purity of the protein was then confirmed by the presence of a single narrow band on SDS-PAGE and a single peak on HPLC.

The biological activity of the beta IL-1 obtained by the method of the present invention was determined by the test described by Kaye et al. (J. Immunol., 13, 1339–1345, 1984) with the use of recombinant beta IL-1 isolated from *E.coli*, with a specific activity of $8.5 \times 10^8$ U/mg of protein, as the standard.

As shown in FIG. 9, the beta IL-1 showed a biological activity equivalent to that of the standard.

The human beta interleukin-1 obtained by the method of the present invention can then be used for the treatment of autoimmune diseases and the activation of repair mechanisms in cases of tissue damage.

Moreover, it can be used as an adjuvant in the formulation of vaccines.

The beta IL-1 thus produced can be administered to man for the clinical uses mentioned above by conventional techniques such as, for example, intramuscular, intravenous and subcutaneous injection.

Naturally, the dose required may vary according to the condition to be treated, the gravity of the case, the duration of the treatment and the method of administration.

A form suitable for pharmaceutical use may be obtained by the reconstitution of lyophilised beta IL-1 in a sterile solution before use.

Stabilising buffers, bacteriostatic substances and other additives may be added to the pharmaceutical compositions.

In accordance with the present invention, the plasmids pSM 308 and pSM 320 were deposited at the American Type Culture Center the former as *B.subtilis* SMS 118 (pSM308) ATCC 68047.

BRIEF DESCRIPTION OF THE DRAWINGS

FIG. 4: shows the nucleotide sequence of the subtilisin secretion signal (SEQ.ID. No. 2).

Figure 1:
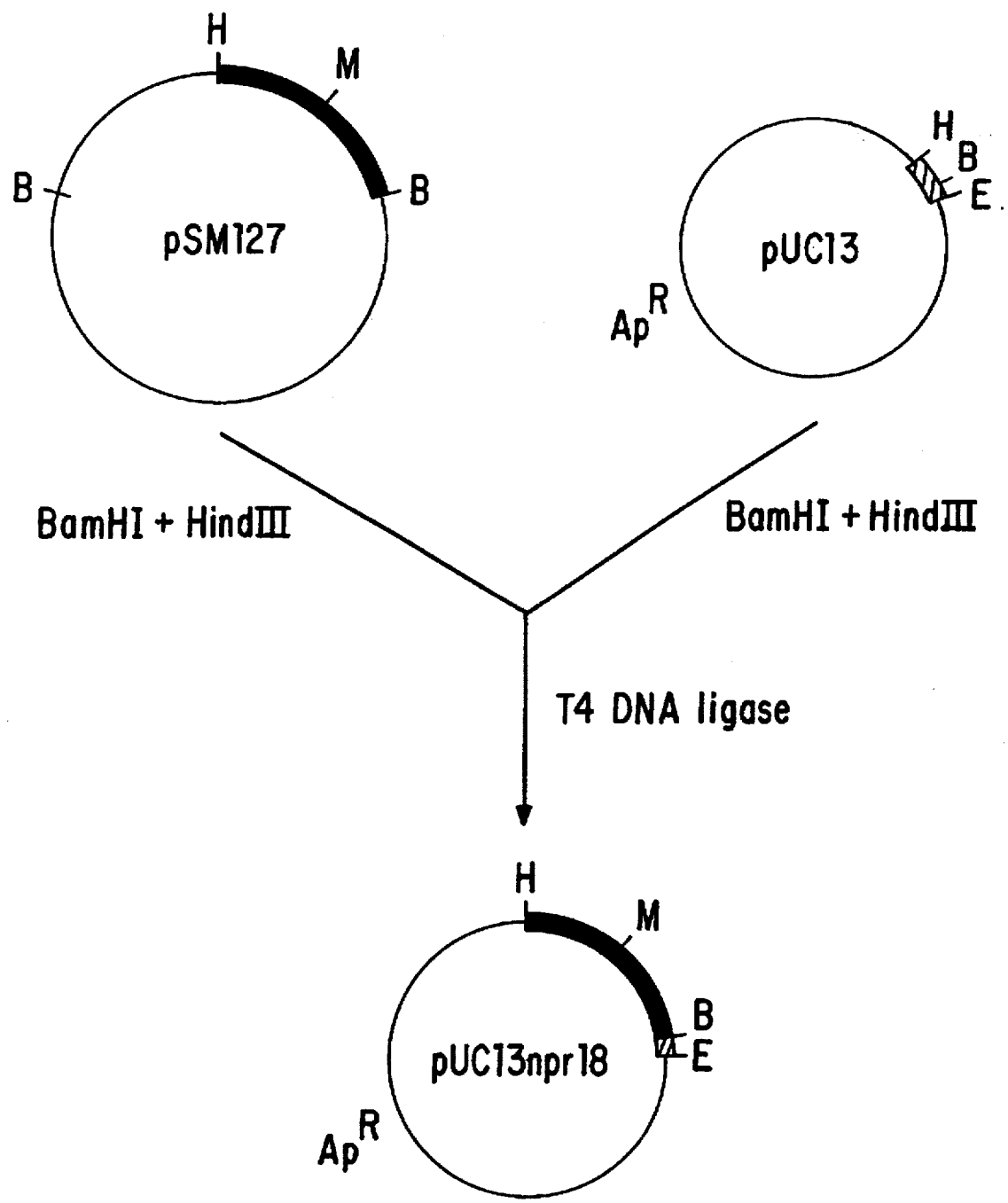
FIG. 1: shows the construction of the plasmid pUC 13 npr 18.

The following experimental examples are illustrative and non-limiting of the invention.

EXAMPLE 1

Construction of the vector pSM 308 with expression in *B.subtilis*.

a) Isolation of the npr promoter

10 µg of the plasmid pSM 127 NRRL-B 15900 were suspended in 100 µl of 50 mM, pH 7.8 Tris-HCl, 10 mM MgCl$_2$, 50 mM NaCl buffer and digested with 10 units (U) of the HindIII and BamHI restriction enzymes (Boehringer), at 37° C. for 1 hour.

The enzymatic reaction was then stopped at 65° C. for 10 minutes and the digestion mixture was loaded on to 0.8% agarose gel and run at 80 volts for about 3 hours.

Upon completion, the Hind III-BamHI fragment with about 1500 bp containing the promoter and the first 200 nucleotides of the neutral protease gene (npr) was eluted as described by Maxam and Gilbert (P.N.A.S., 74, 560, 1977).

100 ng of the fragment were ligated with 100 ng of the vector pUC 13 (Boehringer), previously digested with the restriction enzymes HindIII and BamHI, in 20 µl of ligation mixture containing 66 mM, pH 7.6 Tris-HCl, 1 mM ATP, 10 mM MgCl$_2$, 10 mM dithiothreitol (DTT). The reaction was carried out in the presence of 1U of T4 DNA ligase at 14° C. for 16 hours.

The mixture was then used to transform cells of *E.coli* JM 101 (BRL) made competent with 50 mM CaCl$_2$ (Mandel, M. and Higa, 1970, J. Mol. Biol. 53, 154) as described by Hanahan, D., 1983, J. Mol. Biol., 166, 557–580.

The transformants were selected on LB agar plates (16 g/l Bacto triptone (DIFCO), 10 g/l NaCl) containing 100 µg/ml of ampicillin, 40 µg/ml of X-Gal (5-bromo-4-chloro-3-indolyl-D-galactopyranoside) and 125 µg/ml IPTG (isopropyl-beta-D-thiogalactopyranoside). With the above method, the white colonies (positive) were easily distinguishable from the non-recombinant blue colonies.

The plasmid pUC 13npr18, containing the 1500-bp fragment including the promoter and the first 200 nucleotides of neutral protease was isolated from one of the positive clones (FIG. 1).

In order to put the human beta IL-1 structural gene under the control of this promoter, suitable restriction sites were created downstream of that region by means of the in vitro mutagenesis method based on the "polymerase chain reaction" technique (Sanger, F. et al., PNAS, 74, 5460–5467, 1977).

More particularly, the 1500-bp insert, whose entire nucleotide sequence was known, was subjected to mutagenesis by the insertion of the EcoRI specific restriction site downstream of the ribosomal binding site (RBS) and the removal of the first 200 nucleotides of the neutral protease gene.

For this purpose, an oligonucleotide was synthesised, with a 3' end complementary to the protease RBS and a non-complementary 5' end modified so as to contain the recognition site for the EcoRI restriction endonuclease.

This oligonucleotide, which was synthesised by known methods by means of a System One Plus DNA Synthesizer (Beckman), has the sequence (SEQ.ID. No. 3):

The second oligonucleotide used as a primer was the "universal primer" (SEQ.ID. No. 4): 3'T G A C C G G C A G C A A A A T G 5' (New England Nuclear) which bonds downstream of the target sequence to be amplified. The subsequent polymerisation reaction gave rise to a final product with approximately 1300 bp without the first 200 nucleotides of the neutral protease and containing the GAATTC sequence recognised by the enzyme Eco RI at its 3' end.

Figure 2:
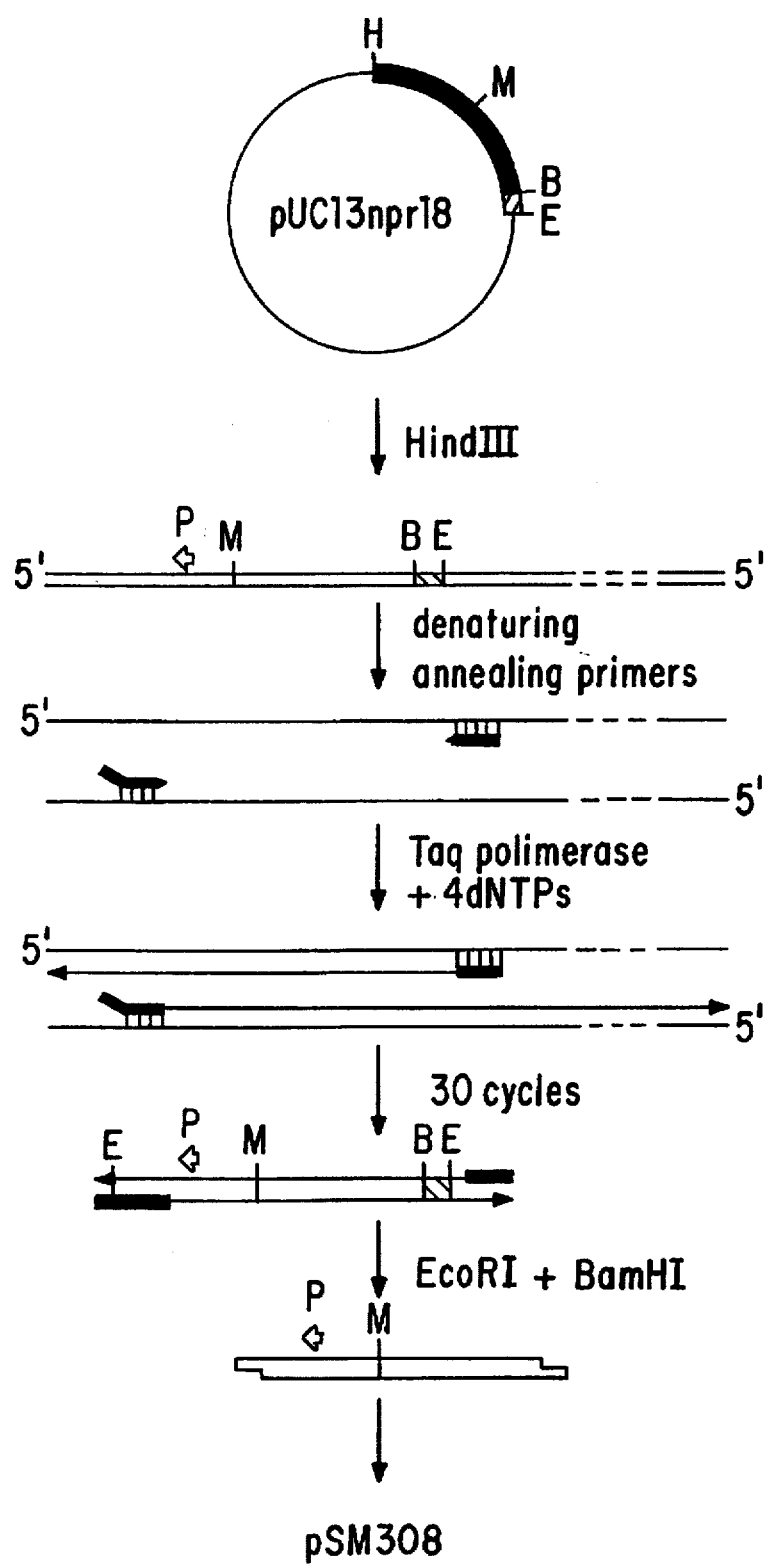
FIG. 2: shows the isolation of the 1300-bp fragment containing the npr promoter and, downstream thereof, the EcoRI restriction site.

In practice, the 1300-bp fragment was constructed by mixing 30 ng of the linearised plasmid pUC 13 npr 18 with the restriction enzyme HindIII, with 100 picomoles of each synthetic oligonucleotide (primer), 200 µM of each of the four desoxynucleotide triphosphates (dATP, dCTP, dGTP, dTTP) and 2U of Taq polymerase (Biolabs). After a denaturing step at 95° C. for 1 minute, the mixture was kept at 40° C. for 2 minutes to enable the two primers to anneal (bond) to the respective helices of the target sequence and, subsequently, at 70° C. for 8 minutes to allow the synthesis of the two new DNA strands starting from the 3' end of the two oligonucleotides (polymerisation) (FIG. 2). The denaturing, annealing and polymerisation cycle was repeated 30 times and produced approximately 4 µg of the target sequence modified as envisaged.

b) The construction of pSM 308

The 1300-bp fragment produced in a), that is, the fragment containing the npr promoter and the sequence recognised by EcoRI at its 3' end, was then used construct of the vector pSM 308.

In practice, 2 µg of the fragment were digested with 2U of each of the enzymes EcoRI and BamHI at 37° C. for 1 hour.

Simultaneously, 10 µg of the plasmid pC 194 (Hironouchi, S. and Weisblum, B., 1982, H. Bacteriol., 150, 2, 815–825) were linearised with 12U of HindIII at 37° C. for 1 hour and then partially digested with 10U of MboI (BRL) at 37° C. for 2 minutes. The reaction was stopped immediately with 20 mM EDTA (final concentration) and then at 65° C. for 10 minutes.

The 2400-bp HindIII-MboI fragment, including the CAT gene and the replication origin which functions in B. subtilis was then isolated on 0.8% agarose gel.

Finally, 50 µg of the vector pUC 12 (Boehringer) were digested with 70 units of each of the two restriction enzymes EcoRI and HindIII (Boehringer) at 37° C. for 1 hour in 400 µl of reaction mixture. The 50-bp DNA fragment which constitutes the multiple cloning site (m.c.s) of pUC 12 was then isolated on 0.8% polyacrylamide gel.

The three fragments were then mixed in a molar ratio of 1:1:1 to a final concentration of 100 µg/ml, in 5 µl of 1 mM ATP, 20 mM pH 7.6 Tris-HCl, 10 mM MgCl$_2$ and 10 mM DTT containing 2U of T4 DNA ligase. The reaction was carried out at 14° C. for one night.

The entire ligation mixture was then used to transform cells of B.subtilis SMS 118 (rec$^+$, npr$^-$, spr$^-$) made competent by the method described by Contente and Dubnau (Mol. Gen. Genet. 167, 251–258, 1979).

Figure 3:
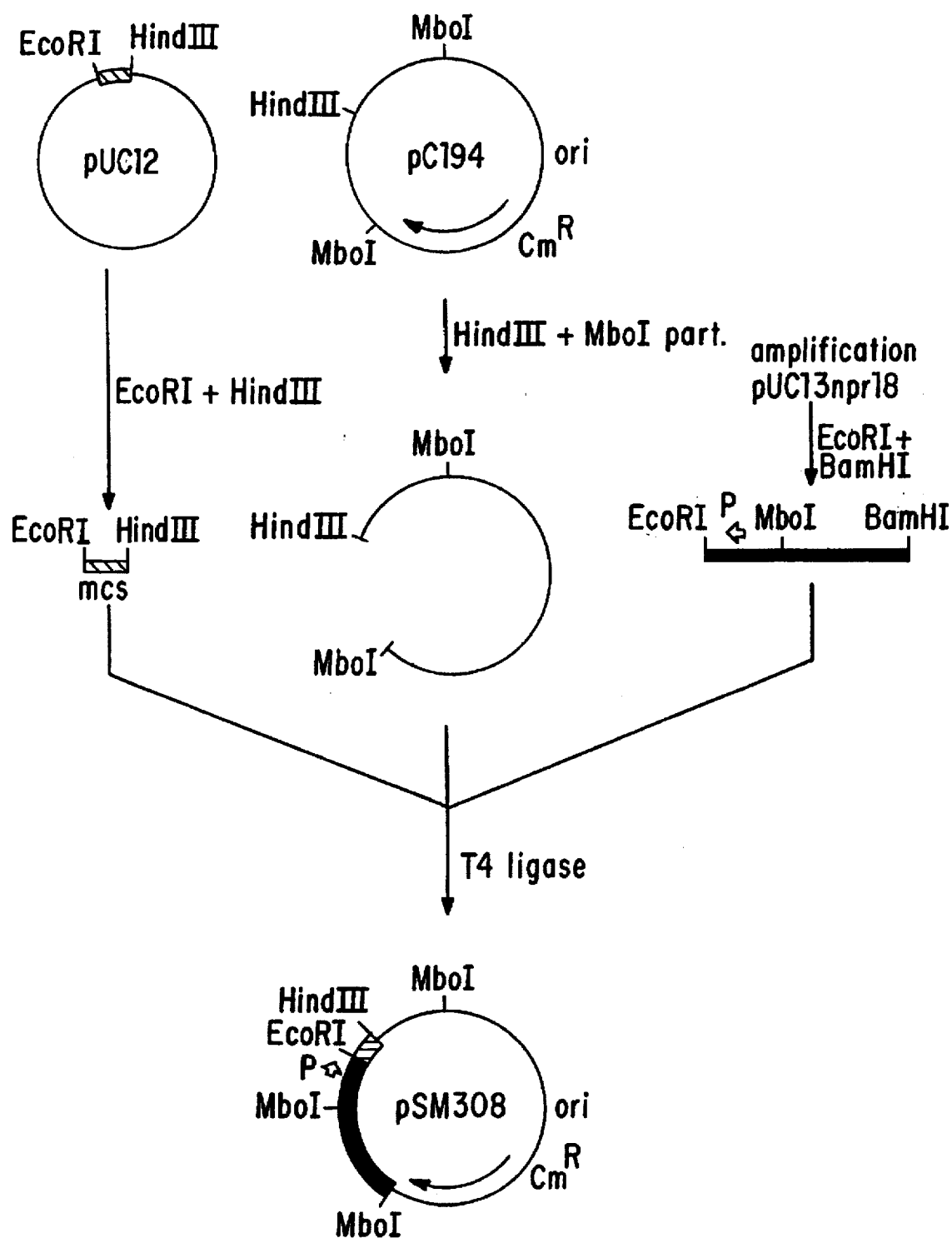
FIG. 3: shows the construction of the plasmid pSM 308.

The recombinant clones were selected on TBAB (DIFCO) plates containing 5 µg/ml of chloramphenicol (Cm). A plasmid containing approximately 3750 bp, including the npr promoter and, downstream thereof, the EcoRI specific site and the mcs of pUC 12, was isolated from one of the positive clones (Cm$^R$). This expression vector, termed pSM 308 (FIG. 3), can replicate in B.subtilis and contains the npr promoter which is active in the stationary growth phase. Moreover, downstream of the npr RBS, it carries numerous specific restriction sites useful for the cloning of heterologous genes.

EXAMPLE 2

Construction of the plasmid pSM 320 for the secretion of human beta IL-1 by B.subtilis cells.

a) The construction of the pUC 13 Ls beta IL-1 vector

The subtilisin leader used for the secretion of the beta IL-1, was designed so that its 5' end was compatible with that generated by the EcoRI restriction enzyme and its 3' end was exposed and lacking the last 12 nucleotides which constitute the cleavage site proper. This leader, synthesised by the System One Plus Synthesizer (Beckman), has the sequence shown in FIG. 4.

Simultaneously, the plasmid pUC 13 was digested with the enzymes EcoRI and PstI (Boehringer) at 37° C. for 1 hour under the conditions suggested by the supplying company. The 2700-bp DNA fragment thus obtained was isolated on 0.8% agarose gel.

10 µg of the fragment were then ligated with 3 µg of the leader sequence in 10 µl of ligation mixture in the presence of 1U of T4 DNA ligase at 14° C. for one night. The enzymatic reaction was stopped at 65° C. for 10 minutes and the resulting mixture was digested with 15U of PstI in order to eliminate any dimers formed during the ligation reaction. The 2780-bp monomer thus obtained was designated A DNA.

3 µg of the plasmid pSM 261 ATCC 67743 containing the human beta IL-1 structural gene were linearised with 3U of EcoRI restriction enzyme which cuts immediately upstream of the ATG codon which initiates translation of the beta IL-1 sequence. The linearised plasmid DNA was then treated with 1U of Bal 31 exonuclease (Boehringer) in 40 µl of reaction mixture at 23° C. for 15 seconds. The reaction was stopped by the addition of 20 mM EDTA and the DNA was precipitated with ethanol at –80° C. After separation by centrifuging (Eppendorf centrifuge model 5450, at 10,000 rpm for 10 minutes, at 4° C.), the DNA was treated under standard conditions at 37° C. for 2 minutes with 1.2U of ExoIII which hydrolyses the molecule starting from the 3' end.

The enzyme was then deactivated with phenol-chloroform/chloroform-isoamyl and the DNA was precipitated with ethanol.

These enzymatic treatments eroded the 5' portion of the gene which codes for beta IL-1 (and hence the ATG triplet) and exposed the 5' end as a single helix. After this treatment, the DNA was digested with 3U of PstI which cuts downstream of the beta IL-1 gene. The 630 bp DNA fragment thus generated, called B DNA, was isolated on 0.8% agarose gel.

A single-strand, 36-base oligonucleotide which can act as a bridge between the exposed 3' and 5' ends of the A and B DNA and contains the 12 nucleotides which correspond to the cleavage site of the subtilisin leader was then synthesised.

The oligonucleotide has the sequence (SEQ.ID. No. 1):

```
                              ala
3'CGTTGTACAGACGCGTCCGGCGTGGACATGCTAGTG 5'
  sub.     leader       +1    beta IL-1
```

100 ng of A DNA, 80 ng of B DNA and 20 ng of the synthetic oligonucleotide were then ligated in 20 µl of 20 mM pH 7.6 Tris-HCl, 10 mM MgCl$_2$, 10 mM DTT, 1 mM ATP buffer solution in the presence of 1 unit of T4 DNA ligase at 14° C. for 16 hours.

Figure 5:
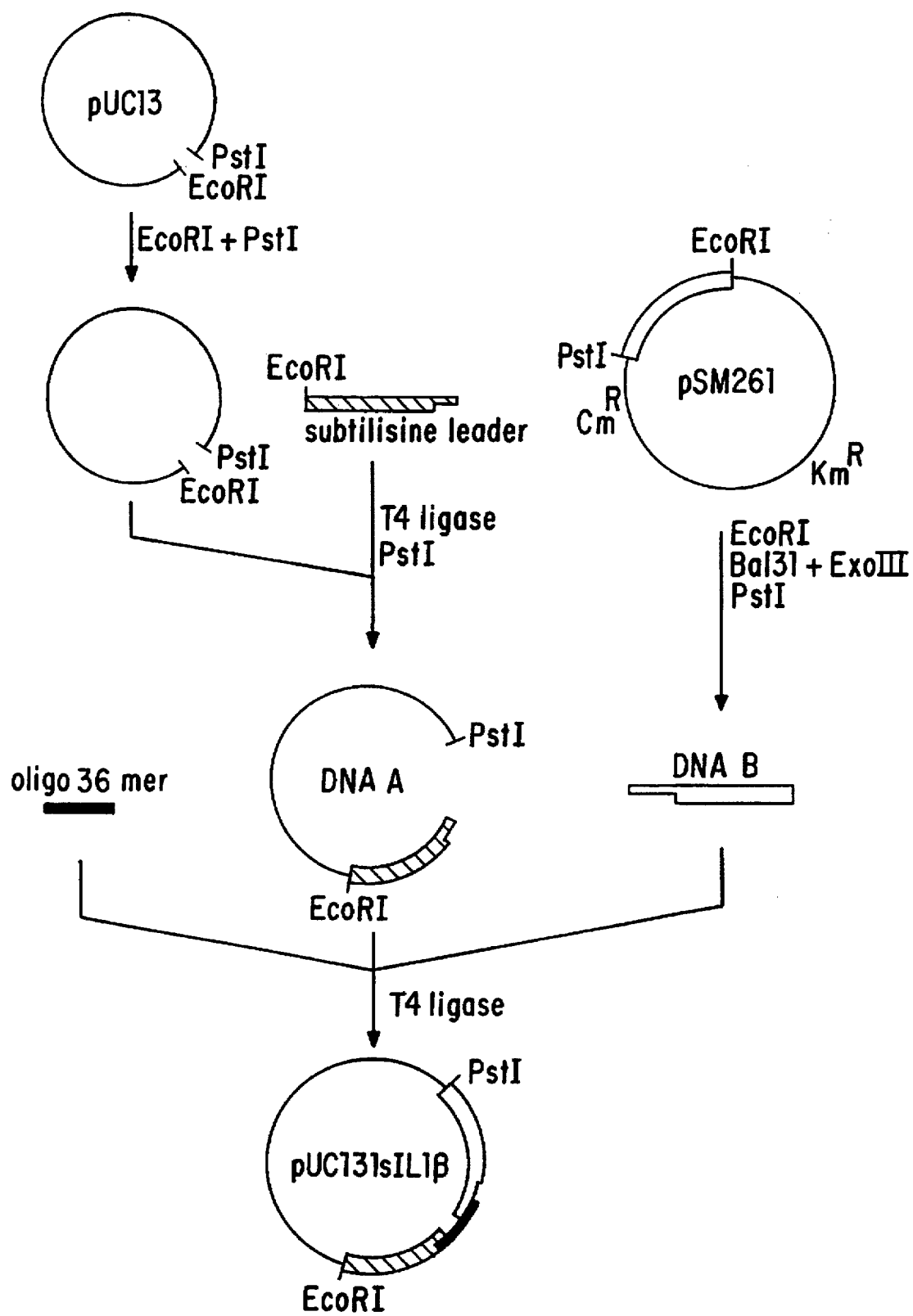
FIG. 5: shows the construction of the intermediate plasmid pUC 13 Ls beta IL-1.

The ligation mixture was then used to transform competent E.coli JM 101 cells and the recombinants were selected on LB agar plates to which 100 µg/ml of ampicillin, 40 µg/ml C-Gal and 125 µg/ml of IPTG had been added. A plasmid containing approximately 3480 bp was extracted from a positive (white) clone and, as confirmed by enzymatic digestion and sequence analysis, contained the beta IL-1 gene, immediately preceded by the subtilisin leader. This plasmid, hereinafter indicated pUC 13 Ls beta IL-1, is shown in FIG. 5.

b) Construction of the plasmid pSM 320

The plasmid pUC 13 LS beta IL-1 (1 µg) was digested with 1U of Eco RI and Pst I at 37° C. for 1 hour. The 700 bp fragment containing the gene which codes for mature beta IL-1, preceded by the subtilisine leader sequence, was then isolated on 0.8% agarose gel. This fragment (400 ng) was then ligated with the plasmid pSM 308 (1 µg) digested with the same enzymes in 10 µl of ligation mixture containing 1 unit of T4 DNA ligase, at 14° C. for one night.

The mixture was used to transform competent cells of B.subtilis SNS 118 and the transformants were selected on TBAB (DIFCO) plates containing 5 µg/ml of chloramphenicol.

Figure 6:
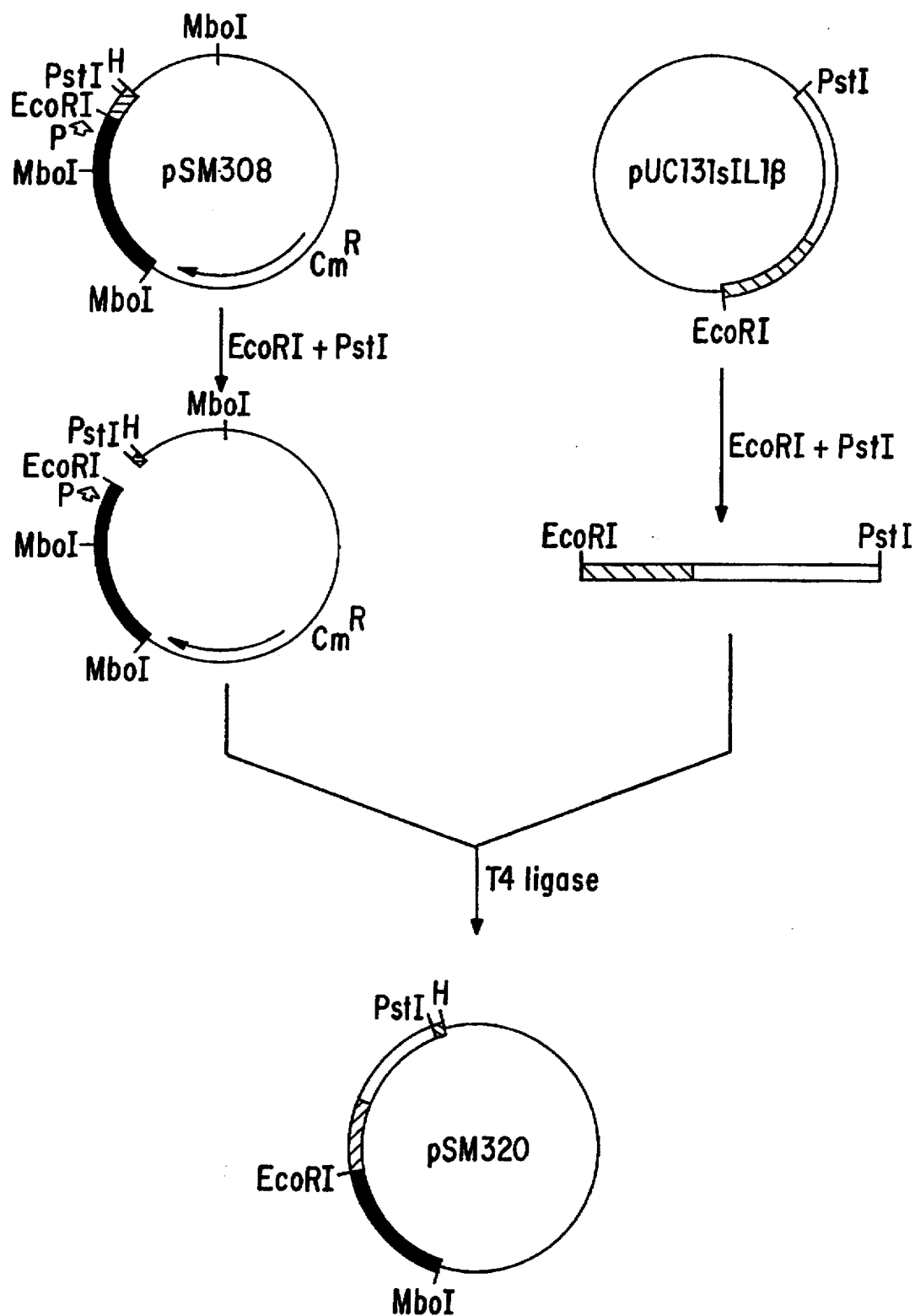
FIG. 6: shows the construction of the plasmid vector pSM 320.

A plasmid was isolated from a positive clone and contained, approximately 4510 bp including the beta IL-1 gene fused to the subtilisin leader sequence and put under the control of the npr promotor, as confirmed by analysis of its nucleotide sequence by the method of Sanger, F. et al. (PNAS USA, 74, 5460–5467, 1977). This plasmid, indicated pSM 320, is shown in FIG. 6.

EXAMPLE 3

The extracellular expression of mature beta IL-1 by *B. subtilis* cells

*B.subtilis* SMS 118 (pSM 320) cells were grown in 10 ml of VY broth (Veal Infusion Broth) (DIFCO) containing 5 µg/ml of chloramphenicol at 37° C. for one night.

At the end of this period, 1 ml of the culture was centrifuged at 15,000 rpm at 20° C. for 5 minutes and the extracellular proteins were isolated from the cell-free supernatant liquor, whilst the intracellular proteins were extracted from the cell pellet.

In practice, 100 µl of 50% trichloroacetic acid (TCA) were added to 900 µl of the supernatant liquor and the resulting mixture was incubated in ice for 1 hour and then centrifuged for 10 minutes at 4° C. The proteinaceous pellet thus obtained was washed with cold acetone and then resuspended in a buffer ("loading buffer") having the following composition: 125 mM pH 6.8 Tris-HCl, 3% sodium dodecyl sulphate (SDS), 20% glycerol, 3% beta-mercaptoethanol and 0.025% bromophenol blue.

20 µl of the mixture, corresponding to 100 µl of supernatant liquor, were denatured by heating (100° C.) and loaded on to 12.5% polyacrylamide-SDS gel.

Figure 7A:
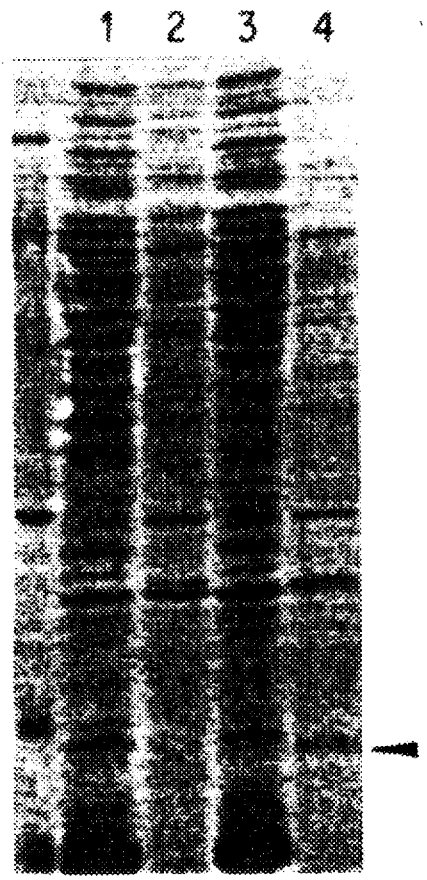
FIG. 7: acrylamide-SDS gel after staining with Coomassie blue (A) and an immunoblot (B) of the proteinaceous extracts of *B.subtilis* SMS 118 (pSM 308) and *B.subtilis* SMS 118 (pSM 320).
Figure 7B:
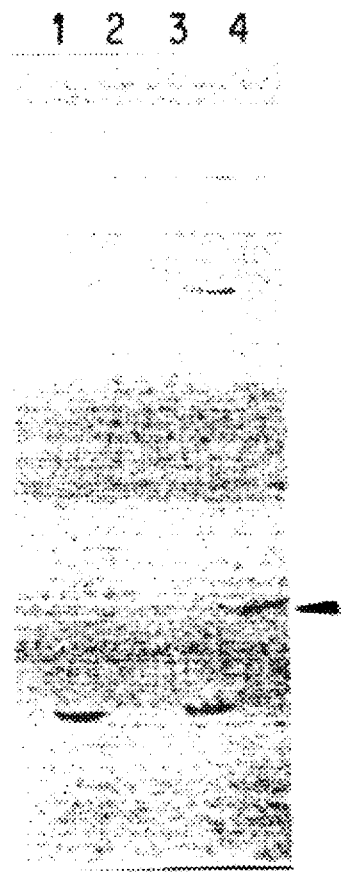

In parallel, the cell pellet, washed in SET buffer (20% sucrose, 30 mM pH 7.6 Tris-HCl, 1 mM EDTA) was suspended in 100 µl of the same washing buffer containing 1 mg/ml of lysozyme and incubated at 37° C. for 15 minutes in order to break down the cell walls. After the addition of "loading buffer" (150 µl), 20 µl of extract, corresponding to 100 µl of culture, were denatured at 100° C. and loaded onto 12.5% SDS-polyacrylamide gel. After electrophoresis at 20 mA for approximately 3 hours, the proteinaceous bands on the two gels were made visible by staining with Coomassie blue transferred in parallel on to nitrocellulose filters (Schlecher and Schull 45 µm) and treated with rabbit anti-recombinant beta IL-1 antibodies (Sclavo) and goat anti-rabbit antibody antibodies complexed with peroxidase (Miles). After staining with Coomassie blue (FIG. 7A) the presence, in the supernatant liquor, of a band with a molecular weight of 17,500 Daltons (dish 4) corresponding to mature beta IL-1 was clearly seen. This band was absent from the intra- and extra-cellular extracts of the *B.subtilis* SMS 118 (pSM 308) control strain (dishes 1 and 2 respectively) and from the intracellular proteinaceous extract obtained from the *B.subtilis* SMS 118 (pSM 320) cells (dish 3). The Western blot test with anti-beta IL-1 polyclonal antibodies which react specifically against this proteinaceous band confirms this result (FIG. 7B).

With the use of the method of the present invention, 100% of the beta IL-1 was secreted in the mature, non-degraded form.

EXAMPLE 4

The purification of secreted beta IL-1

*B.subtilis* SMS 118 (pSM 320) cells were grown in a MULTIGEN TN New Brunswick fermenter containing 1.2 l of VY broth to which 40 g/l of maltose and 5 mg/l of chloramphenicol had been added. The fermentation was carried out under controlled pH conditions (6.8) at 1000 revolutions per minute, 0.5 V/V air/minute, at 37° C. for 30 hours. At the end of this period, the culture was centrifuged as described in Example 3 and gave 1.12 l of supernatant liquor. The protein was then precipitated with 85% cold $(NH_4)_2SO_4$ for 1.5 hours. The precipitate obtained was separated by centrifuging at 8,000 rpm for 10 minutes and then resuspended in 20 mM pH 7.5 Tris-HCl buffer containing 1 mM PMSF (phenylmethane sulphonyl fluoride). The resulting solution was dialysed for 16 hours against the same buffer. 90 ml of a mixture with a total protein content of 3.39 mg/ml were obtained. The solution was then loaded into a 2.6×40 cm DEAE-cellulose column (DE-52 Whatmann), equilibrated in 20 mM pH 7.5 Tris-HCl and eluted with the same buffer at a flow rate of 50 ml/hour.

The elution was monitored continuously at an absorbance of 280 nm.

The fractions containing the beta IL-1 were collected and examined electrophoretically on SDS-PAGE (Laemmli, Nature, 227, 680–685, 1970).

Those containing beta IL-1 (fractions 18–27) which showed a single narrow band, were combined to yield 186 ml of a solution with a proteinaceous content of approximately 71 µg/ml.

The solution was then concentrated on YM-5 membrane (Amicon) until 5.9 ml of a solution containing 1.9 mg/ml of protein were obtained.

Figure 8A:
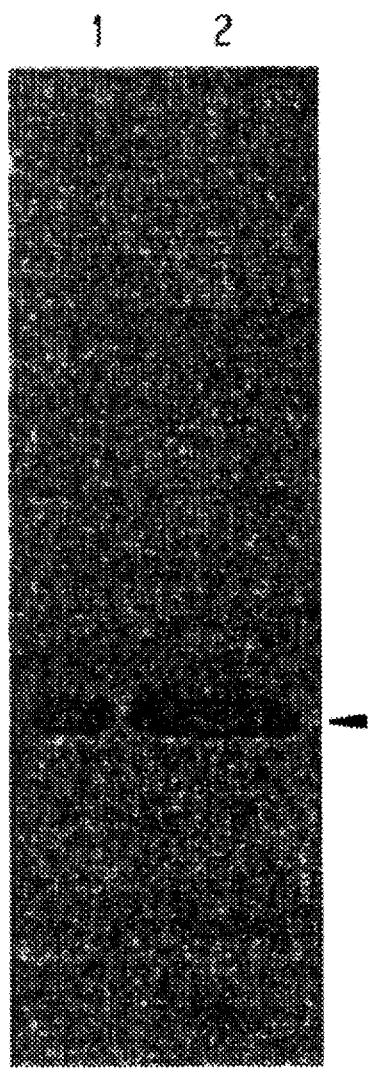
FIG. 8: acrylamide-SDS gel (A) and an immunoblot (B) of the purified beta IL-1 secreted by *B.subtilis* SMS 118 (pSM 320) and of the standard.
Figure 8B:
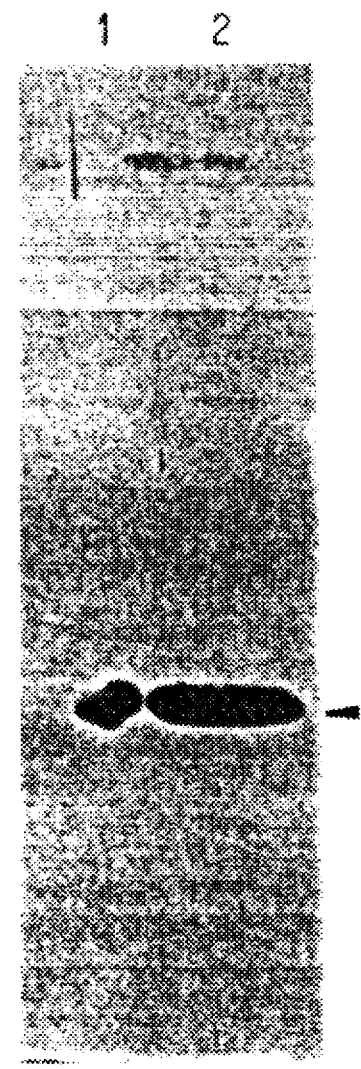

The beta IL-1 was further purified in a 1×9 cm Red-Sepharose column (Pharmacia, Uppsala), equilibrated with 4 mM pH 7.5 Tris-HCl. The protein was eluted with an NaCl gradient of from 0 to 1M in 20 mM pH 7.5 Tris-HCl. The fractions containing beta IL-1 were recovered and concentrated as described above. A total of 4.4 mg of protein with a purity of 90% were obtained. The purity of the beta IL-1 was confirmed by electrophoresis on 12.5% SDS-acrylamide gel and by immunoblot (FIGS. 8A and B, dish 2) and compared with the standard beta IL-1 (dish 1).

The amino acid analysis of the protein showed the correct sequence, confirming that it had been processed correctly.

EXAMPLE 5

Analysis of the specific activity of secreted beta IL-1

Figure 9:
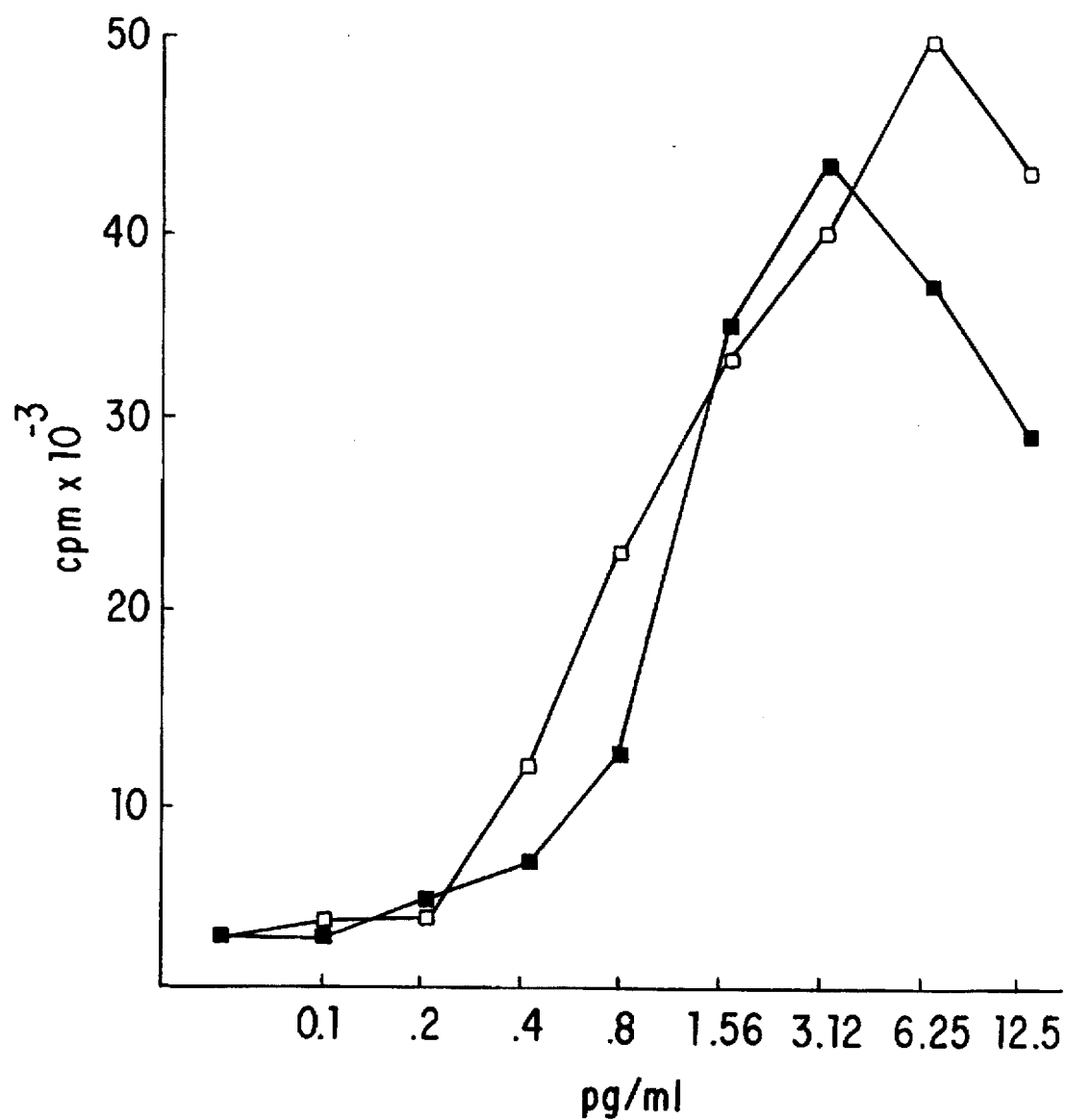
FIG. 9: a graph corresponding to the specific activity of extracellular beta IL-1 purified from *B.subtilis* compared with standard beta IL-1.

The specific acitivty of beta IL-1 purified as described in Example 4 above was determined by the test described by Kaye et al. (J. Immunol., 133, 1339–1345, 1984). In practice, D10 G.4.1 cells (SCLAVO) were spread ($2\times10^4$/dish) in each dish of a cluster plate of 96 flat-bottomed dishes (Costar, Cambridge, Mass.) in RPMI-1640 culture medium (GIBCO, Grand Island, N.Y.) containing 25 mM HEPES, 50 µg/ml gentamycin, 2 mM L-glutamine, 10% incomplete bovine foetal serum (HyClone Sterile Systems, Logan, Utah) and $6\times10^{-5}M$ 2-mercaptoethanol. Triple graduated doses of standard recombinant beta IL-1 (Sclavo) and of the sample, diluted in the same medium, were added to the dishes. The final volume in each dish, after the addition of ConA (Concanavaline A) to a final concentration of 2.5 µg/ml, was 0.2 ml. After incubation at 37° C. in a humid environment with 5% $CO_2$ for 48 hours, 0.5 µCi of tritiated thymidine (Amersham, specific activity 2 µCi/mmole) were added to each microdish in order to measure the cell proliferation. After 16–18 hours, the cells were collected from the dishes by means of a multiple cell harvester (Skatron, Lier, Norway) and the radioactivity incorporated by the proliferating cells was evaluated by liquid scintillation. As shown in FIG. 9, the maximum incorporation of marked thymidine in the D10 G.4.1 cells was achieved with the addition of 6.25 pg/ml of purified beta IL-1. The specific activity of the protein, which was $1\times10^9$, is comparable with that of the standard.

SEQUENCE LISTING

SEQ ID NO: 1
SEQUENCE TYPE: Nucleotide
SEQUENCE LENGHT: 36 base pairs
STRANDEDNESS: Single
TOPOLOGY: Linear
MOLECULE TYPE: Synthetic
FEATURES: From 16 to 1 complementary to the first 5
codons of IL-1β; from 36 to 17 complementary to the last
6 codons of subtilisin leader sequence.

```
GTGATCGTAC AGGTGCGGCC TGCGCAGACA TGTTGC                    36
```

SEQ ID NO: 2
SEQUENCE TYPE: Nucleotide with corresponding protein
SEQUENCE LENGHT: 82 base pairs
STRANDEDNESS: Both single and double
TOPOLOGY: Linear
MOLECULE TYPE: Synthetic
FEATURES: from 8 to 82 first amino acid of subtilisin
signal peptide

```
AATTCTT ATG AGA AGC AAA AAA TTG TGG ATC AGC TTG TTG        40
        Met Arg Ser Lys Lys Leu Trp Ile Ser Leu Leu

TTT GCG TTA ACG TTA ATC TTT ACG ATG GCA TTC AGC AAC        79
Phe Ala Leu Thr Leu Ile Phe Thr Met Ala Phe Ser Asn

ATG
Met
```

SEQ ID NO: 3
SEQUENCE TYPE: Nucleotide
SEQUENCE LENGHT: 37 base pairs
STRANDEDNESS: Single
TOPOLOGY: Linear
MOLECULE TYPE: Synthetic
FEATURES: from 7 to 13 EcoRI site

```
AGCTTAAGAA TTCCCCCTTT TTGAAAATAC TGAAAAC                   37
```

SEQ ID NO: 4
SEQUENCE TYPE: Nucleotide
SEQUENCE LENGHT: 17 base pairs
STRANDEDNESS: Single
TOPOLOGY: Linear
MOLECULE TYPE: Synthetic
PROPERTIES: Universal Primer

```
GTAAAACGAC GGCCAGT                                         17
```

I claim:

1. A *Bacillus subtilis* plasmid vector for expressing heterologous genes which code for proteins of interest comprising: (1) CAT, a gene which codes for resistance to chloramphenicol; (2) *Bacillus subtilis* neutral protease promoter; (3) *Bacillus subtilis* neutral protease ribosome binding site; and immediately downstream from said ribosome binding site; (4a) an Eco RI restriction site; and 4(b) a $pUC_{12}$ multiple cloning site.

2. A plasmid vector according to claim 1, deposited as *Bacillus subtilis* SMS 118 (pSM 308) ATCC 68047.

3. A plasmid vector according to claim 1, further comprising a *Bacillus subtilis* serine protease signal sequence operatively linked to the heterologous gene.

4. A *Bacillus subtilis* transformed with the plasmid vector of claim 1.

5. A *Bacillus subtilis* transformed with the plasmid vector of claim 2.

6. A *Bacillus subtilis* transformed with the plasmid vector of claim 3.

* * * * *